United States Patent

Buchholtz et al.

[11] Patent Number: 5,697,897
[45] Date of Patent: Dec. 16, 1997

[54] ENDOSCOPE CARRYING A SOURCE OF THERAPEUTIC ULTRASOUND

[75] Inventors: Gerhard Buchholtz, Erlangen; Ulrich Schaetzle, Roettenbach, both of Germany

[73] Assignee: Siemens Aktiengesellschaft, Munich, Germany

[21] Appl. No.: 369,392

[22] Filed: Jan. 6, 1995

[30] Foreign Application Priority Data

Jan. 14, 1994 [DE] Germany ................ 44 00 983.6

[51] Int. Cl.⁶ ................ A61B 17/00; A61B 8/12
[52] U.S. Cl. ................ 604/22; 128/660.03; 128/662.06; 607/97; 601/4; 600/103; 600/113; 600/160
[58] Field of Search ................ 600/103, 109, 600/113, 130, 160, 170; 601/2–4; 607/97; 604/22; 128/662.06, 660.03; 606/128

[56] References Cited

U.S. PATENT DOCUMENTS

| 4,327,738 | 5/1982 | Green et al. ................ 128/660 |
| 4,605,009 | 8/1986 | Pourcelot et al. . |
| 4,718,406 | 1/1988 | Bregman et al. . |
| 4,763,662 | 8/1988 | Yokoi ................ 128/660 |
| 4,992,902 | 2/1991 | Wuchinich et al. ................ 604/22 |
| 5,014,708 | 5/1991 | Hayashi et al. . |
| 5,391,140 | 2/1995 | Schaetzle et al. . |
| 5,391,144 | 2/1995 | Sakurai et al. . |
| 5,405,318 | 4/1995 | Nita ................ 604/22 |
| 5,435,304 | 7/1995 | Oppelt et al. . |
| 5,435,805 | 7/1995 | Edwards et al. ................ 604/22 |
| 5,438,997 | 8/1995 | Sieben et al. . |
| 5,456,689 | 10/1995 | Kresch et al. ................ 606/180 |
| 5,471,988 | 12/1995 | Fujio et al. . |
| 5,474,071 | 12/1995 | Chapelon et al. . |
| 5,492,126 | 2/1996 | Hennige et al. . |
| 5,556,377 | 9/1996 | Rosen et al. ................ 604/22 |
| 5,558,092 | 9/1996 | Unger et al. . |

FOREIGN PATENT DOCUMENTS

| 2 543 817 | 10/1984 | France . |
| 77 05 947 | 6/1977 | Germany . |
| 31 41 022 | 4/1983 | Germany . |
| 33 09 096 | 9/1983 | Germany . |

Primary Examiner—Marvin M. Lateef
Assistant Examiner—Shawna J. Shaw
Attorney, Agent, or Firm—Hill, Steadman & Simpson

[57] ABSTRACT

An endoscope includes a carrier which can be inserted into a living examination subject, having a distal end which is advanced into the subject, the carrier carrying an optical examination apparatus by means of which an image from the interior of the subject can be obtained and transmitted to the exterior of the subject, and the carrier also carrying a source of therapeutic ultrasound at the distal end. A body region exhibiting a pathology which is treatable with therapeutic ultrasound can thus be insonified with the therapeutic ultrasound in the same surgical intervention which is used to obtain the endoscopic images.

10 Claims, 3 Drawing Sheets

ENDOSCOPE CARRYING A SOURCE OF THERAPEUTIC ULTRASOUND

BACKGROUND OF THE INVENTION

1. Field of the Invention

The invention is directed to a endoscope having optical examination capability.

2. Description of the Prior Art

Endoscopes are utilized in order to inspect the inside of the body of a patient. Such an examination can supply critical, additional information compared to non-invasive examination methods (for example, x-ray or ultrasound examinations), because the body region of interest can be directly observed. When pathological modifications are suspected, there is the possibility of, for example, taking tissue samples immediately under endoscopic supervision or producing ultrasound images of the affected region given the use of an endoscope having an integrated diagnostic ultrasound applicator.

When a surgical intervention proves necessary, then there is the possibility in many instances of implementing the surgery with minimum invasiveness under endoscopic supervision, namely in the form of an ectomy or resection dependent on the case. Although such minimally invasive operations stress the patient to less of an extent than conventional surgical methods, it would nonetheless be desirable to be able to employ even less stressful treatment methods in some cases.

In this context, German Utility Model 77 05 947 discloses an endoscope to whose proximal end an ultrasound transducer is attached, an ultrasound conductor being connected to the latter and serving the purpose of transmitting the ultrasound waves generated with the ultrasound transducer onto a calculus to be disintegrated, for example, a vesical calculus. This endoscope is, however, unsuitable for surgical interventions other than calculus disintegration.

U.S. Pat. No. 4,718,466 discloses an endscope that contains two light waveguides. One waveguide conducts light serving illumination purposes. The other serves observation purposes and also serves the purpose of supplying laser light or ultrasound waves to a region to be treated. There is thus the possibility of acoustically irradiating tumors with therapeutic ultrasound or undertaking surgical interventions using therapeutic ultrasound. The ultrasound intensity available at the distal end of this known endoscope, however, is relatively low due to the losses occurring in the conduction of the ultrasound waves through the light waveguide as well as because of the small cross-sectional area of the light waveguide, so that the treatment lasts an undesirably long time.

German OS 31 41 022 and French Patent 543 817, moreover, both disclose the arrangement of a diagnostic ultrasound transducer, i.e., an ultrasound transducer serving imaging purposes, at the distal end of an endoscope. The diagnostic ultrasound transducer may be fashioned as a phased array and may be capable of emitting and receiving the diagnostic ultrasound in the fashion of a linear scan.

SUMMARY OF THE INVENTION

It is an object of the present invention to provide an endoscope of the type initially cited which administers a gentler treatment method compared to a resection or ectomy of pathological tissue regions, to the extent the clinical evaluation permits, and such that a short treatment duration is nonetheless possible.

This object is inventively achieved in an endoscope containing optical examination means, and a source of therapeutic ultrasound formed by an ultrasound transducer arranged, i.e. the leadlng end, at the distal end/of the endoscope.

In cases of suitable clinical evaluations, thus, a treatment with therapeutic ultrasound can ensue instead of the surgical removal of pathological tissue regions. As a rule, the treatment will exploit the thermal effect of ultrasound. As a rule, the amplitude and the effective duration of the therapeutic ultrasound will be selected such that temperatures beyond 45° are achieved. This leads to a necrotization of the treated tissue regions. Given specific maladies, for example benign tumors, there is also the possibility of dosing the therapeutic ultrasound such that a heating of the tissue to be treated ensues to no more than 45°, with the result that the metabolism of the rumor cells is negatively influenced. This can lead to a reduction in the growth rate of the tumor or even to a decrease of the tumor. With the assistance of the optical examination means contained in the endoscope, it is easily possible to align the endoscope such that the tissue region to be treated is charged with the therapeutic ultrasound. As a consequence of the arrangement of the ultrasound transducer at the distal end of the endoscope, only extremely slight attenuation losses occur in the path of the therapeutic ultrasound from the ultrasound transducer to the region to be treated. Moreover, the surface of the ultrasound transducer effective as the emission face for the therapeutic ultrasound can be larger than the cross-sectional area of the endoscope. High ultrasound intensities can thus be achieved in the region to be treated, so that short treatment durations are possible.

The treatment of tissue with therapeutic ultrasound is known (see, for example H. Kresse, Kompendium Elektromedizin, 3rd Edition, 1982, Siemens AG Berlin and Munich, pp. 231–237). The ultrasound is usually extracorporeally produced. This results in the fact that the dosing of the therapeutic ultrasound is difficult since the acoustic properties of the tissue layers that the ultrasound must traverse on its path to the region to be treated vary greatly from patient to patient. A certain alleviation of this problem is possible given some clinical pictures wherein the ultrasound transducer is brought optimally dose to the region to be treated using natural body paths. In this case, however, tissue layers are still located between the ultrasound transducer and the region to be treated, making the dosing of the ultrasound more difficult. Compared thereto, it is possible in many instances to place the endoscope of the invention such that no disturbing tissue layers are present between the ultrasound transducer and the affected organ or the tissue region to be treated, so that an exact dosing of the therapeutic ultrasound is possible.

In order to assure that a dose of therapeutic ultrasound adequate for achieving the desired therapeutic effect is supplied only to the tissue region to be treated, it is provided in a preferred version of the invention that the ultrasound transducer emits focused therapeutic ultrasound. It is expedient in this context when the focus zone of the therapeutic ultrasound can be displaced relative to the endoscope without a displacement of the endoscope so that larger tissue regions can also be treated. The displacement of the focus zone relative to the endoscope can be realized easily when the ultrasound transducer is fashioned as a phased array in a known way.

An easier and more precise alignment of the endoscope or the source of therapeutic ultrasound, i.e., the ultrasound transducer, relative to a tissue region to be treated can be achieved according to a preferred embodiment of the invention, means for the emission and for the reception of diagnostic ultrasound are provided. Further information in the form, for example, of ultrasound images can then be produced in addition to the information acquired by the optical examination means. In a version of this embodiment the endoscope contains a diagnostic ultrasound transducer for the emission and for the reception of diagnostic ultrasound that is separate from the therapeutic ultrasound transducer. In a version that is especially advantageous because of its simplicity and its low volume requirement, the source of therapeutic ultrasound, i.e., the ultrasound transducer, is optionally activatable for emitting and for receiving diagnostic ultrasound. It is especially expedient in this context when the ultrasound transducer is implemented as a linear array and emits and receives the diagnostic ultrasound for ultrasound imaging in the fashion of a linear scan. Compared to a sector scan, a linear scan can be realized with substantially less outlay and nonetheless supplies adequate information in the present case since the tissue regions to be treated are usually located close to the endoscope or to the ultrasound transducer.

It is likewise advantageous when, according to another version of the invention, the ultrasound imaging ensues with respect to a region containing the focus zone of the therapeutic ultrasound, since the ultrasound images that are then produced contain optimum information with respect to the tissue region to be treated, or under treatment. In this context, the attending personnel are provided with important, additional information when a mark corresponding to the current position of the focus zone is mixed into the ultrasound images produced with the diagnostic ultrasound, since it can then be seen without further difficulty what location would be treated, or is being treated, at the moment of activation of the therapeutic ultrasound.

DESCRIPTION OF THE PREFERRED EMBODIMENTS

Figure 1:
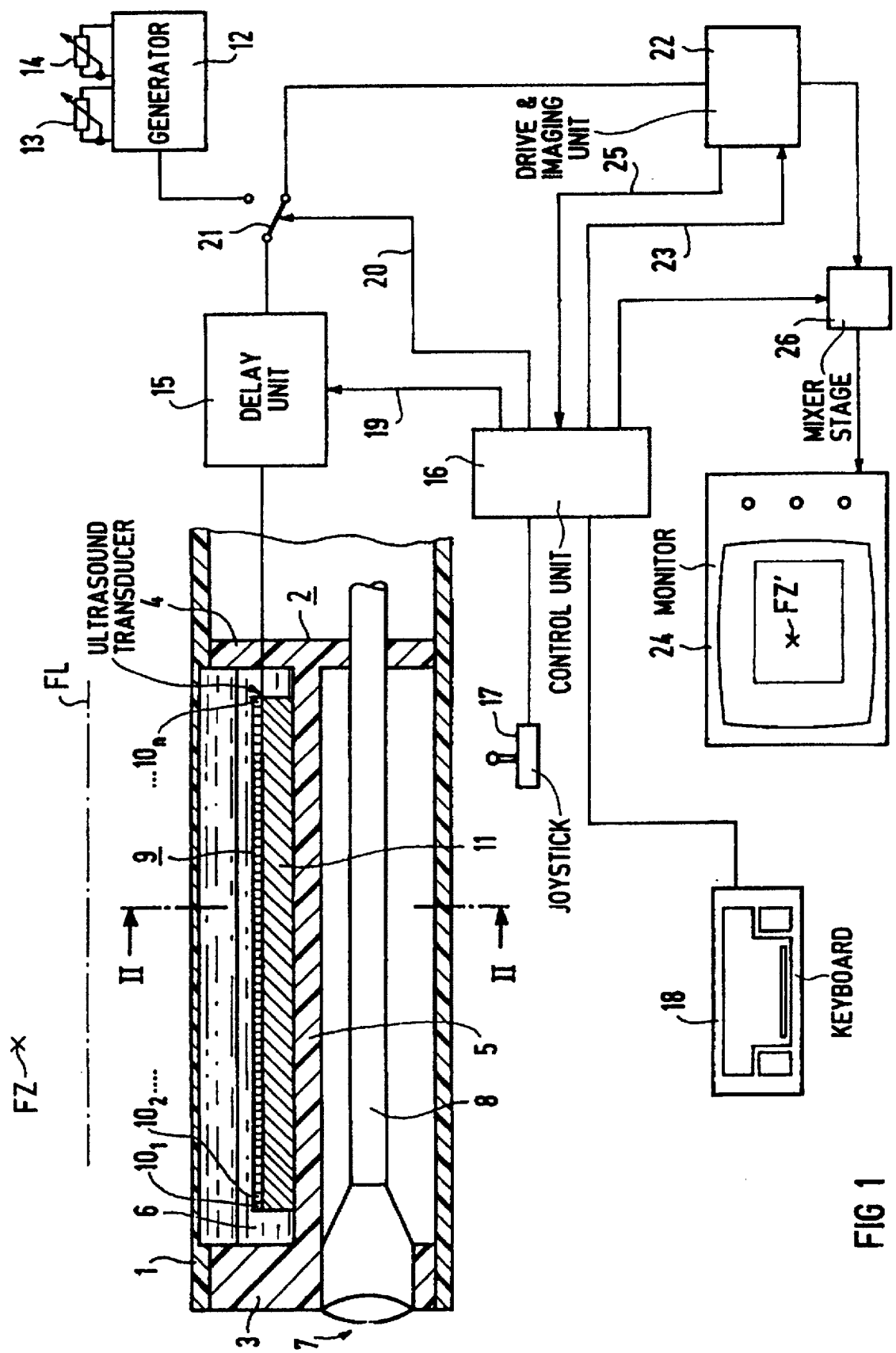
FIG. 1 shows a catheter of the invention shown in a partially sectional, partially schematic block diagram form of presentation.

The distal end of the endoscope of the invention is shown in longitudinal section in FIG. 1. A holder 2 is inserted within a tubular, cylindrical outside wall 1. This holder 2 has two wall parts 3 and 4 connected to one another by a web 5, the wall part 3 being located at the end of the outside wall 1. The holder 2 is introduced into the outside wall 1 such that its wall parts 3 and 4 together with the web 5 terminate a space 6 (shown in FIG. 1) liquid-tight.

An optics 7 is introduced into a bore of the wall part 3 outside the space 6, this optics 7, together with a fiber-optical light waveguide 8, being a component of optical examination means of the type known in conjunction with endoscopes that allow an observer to inspect the inside of the body of the patient when the endoscope is introduced into the interior of the body of the patient.

An ultrasound transducer 9 with which therapeutic ultrasound can be generated is located in the space 6 as a source of therapeutic ultrasound. There is thus the possibility of localizing a tissue region to be examined with the optical examination means and then placing the endoscope by suitable displacement of the endoscope in the advancement or retraction direction so that the therapeutic ultrasound emanating from the ultrasound transducer 9 is incident on the tissue region to be treated.

The ultrasound transducer 9 is composed of a plurality of ultrasound transducer elements $10_1$ through $10_n$ arranged in the fashion of a linear array that are attached in a known way to a backing (carrier member) 11. The backing 11 is connected to the web 5, for example, by gluing.

The emission face of the ultrasound transducer 9, i.e., that surface from which the therapeutic ultrasound proceeds, is thus formed by the sum of the end faces of the ultrasound transducer elements $10_1$ through $10_n$. This emission face is at least of the same size as the cross-sectional area of the endoscope; as may be seen from FIGS. 1 and 2, however, it is preferably larger than the cross-sectional area of the endoscope.

The space 6 is filled with a liquid, for example water, serving as the acoustic propagation medium. In its region lying opposite the ultrasound transducer elements $10_1$ through $10_n$, the outside wall 1 has a reduced wall thickness in order to enable an optimally loss-free passage of the ultrasound waves emanating from the ultrasound transducer 9.

For generating therapeutic ultrasound, the ultrasound transducer 9 is supplied with an alternating current having a suitable frequency and amplitude by a generator 12. The frequency and amplitude are variable, as schematically indicated by two variable resistors 13 and 14 connected to the generator 12.

In order to be able to focus the therapeutic ultrasound onto a focus zone FZ as well as to be able to displace the focus zone FZ relative to the endoscope, the ultrasound transducer 9—which is constructed as a linear array, as already mentioned—is controllable in the fashion of a phased array in a known way. To this end, a delay unit 15 is connected between the ultrasound transducer 9 and the generator means 12. This delay unit 15 supplies the signal supplied from the generator 12 to the individual ultrasound transducer elements $10_1$ through $10_n$ with respective chronological offsets such that a focusing of the therapeutic ultrasound waves emanating from the ultrasound transducer 9 yields a focus zone FZ and the focus zone FZ assumes a desired position.

To this end, the delay unit 15 is driven in the required way by a control unit 16 via a control line 19, whereby the position of the focus zone can be set with a joystick 17 connected to the control unit 16. A possible exemplary position of the focus zone FZ is shown in FIG. 1.

The generating of the signals that drive the individual transducer elements $10_1$ through $10_n$, moreover, can ensue in some other way, for example by a separate oscillator allocated to every transducer element $10_1$ through $10_n$. The oscillators then oscillate with phase shifts relative to one another such that the desired focusing derives.

A keyboard 18 is connected to the control unit 16 in order to be able to execute all other operating events that are required.

Figure 2:
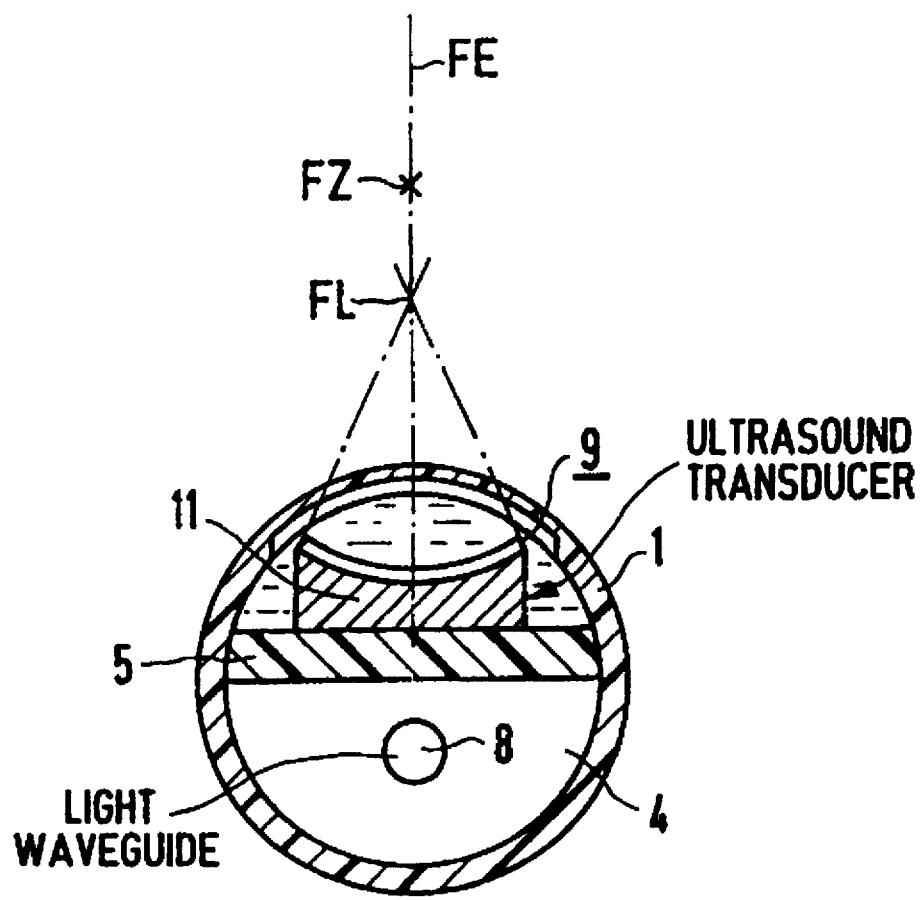
FIG. 2 shows a section taken along line II—II in FIG. 1.

As may be seen from FIG. 2, the surface of the ultrasound transducer 9 is curved cylindrically concave. The ultrasound transducer 9 is thus mechanically pre-focused by this shaping, such that the generated ultrasound waves are theoretically weakly focused onto a focus line FL, which is shown with dot-dash lines in FIG. 1. In reality, however, the waves are weakly focused onto a elongated focus region given drive of all transducer elements $10_1$ through $10_n$ without temporal offset. The described displacement of the focus zone FZ, moreover, ensues in the middle plane FE of the ultrasound transducer 9 corresponding to the plane of the drawing of FIG. 1, this also containing the focus line FL. The intersection line of the middle plane FE with the plane of the drawing lying perpendicular thereto is indicated with a dot-dash line in FIG. 2 referenced FE. A focusing with a lens, moreover, is possible instead of or in addition the described focusing based on mechanical shaping.

In addition to the information acquired via the optical examination means, further information can be acquired by using the ultrasound transducer 9 for generating ultrasound images. To this end, a drive and imaging unit 22 can be connected to the delay unit 15 with a switch 21 actuated by the control unit 16 via a control line 20, instead of being connected to the generator 12.

The drive and imaging unit 22 that is activated by the control unit 16 as needed via a line 23 is conventionally constructed and contains all circuits that are required for collaboration with the ultrasound transducer 9 and the delay unit 15 for generating ultrasound images, the latter then being displayed on a monitor 24. The drive and imaging unit 22, however, does not directly forward the signals for the delay unit 15 thereto but first forwards them via a line 25 to the control unit 16 which then forwards the signals via the line 19 to the delay unit 15.

Differing from the exemplary embodiment shown in the case of FIG. 1, the drive and imaging unit 22 can also have a separate delay unit allocated to it, collaborating with the ultrasound transducer 9 for generating ultrasound images. The drive and imaging unit 22 can then optionally be connected to the ultrasound transducer 9, or to the ultrasound transducer elements $10_1$ through $10_n$ thereof, via a separating circuit, for example suitable filters or switch means.

In the case of the described exemplary embodiment, a linear scan is implemented in a known way for producing ultrasound images. A slice-like body region of the patient is thereby imaged in the ultrasound image, the middle plane thereof corresponding to the middle plane FE of the ultrasound transducer 9. It is thereby assured that the focus zone of the therapeutic ultrasound lies within the region imaged in the ultrasound image.

There is therefore the possibility of mixing a mark FZ' corresponding to the currently set position of the focus zone FZ of the therapeutic ultrasound, set with the joystick 17, into the ultrasound image. To this end, a mixer stage 26 is provided that is supplied with appropriate signals from the control unit 16.

There is also the possibility of first inspecting a body region to be potentially treated with the optical examination means. Following thereupon, there is the possibility of imaging this body region with diagnostic ultrasound and to treat this body region with therapeutic ultrasound as warranted, whereby the positioning of the focus zone FZ of the therapeutic ultrasound corresponding to the respective treatment case can be easily carried out on the basis of the ultrasound image and of the mark FZ' mixed therein.

Figure 3:
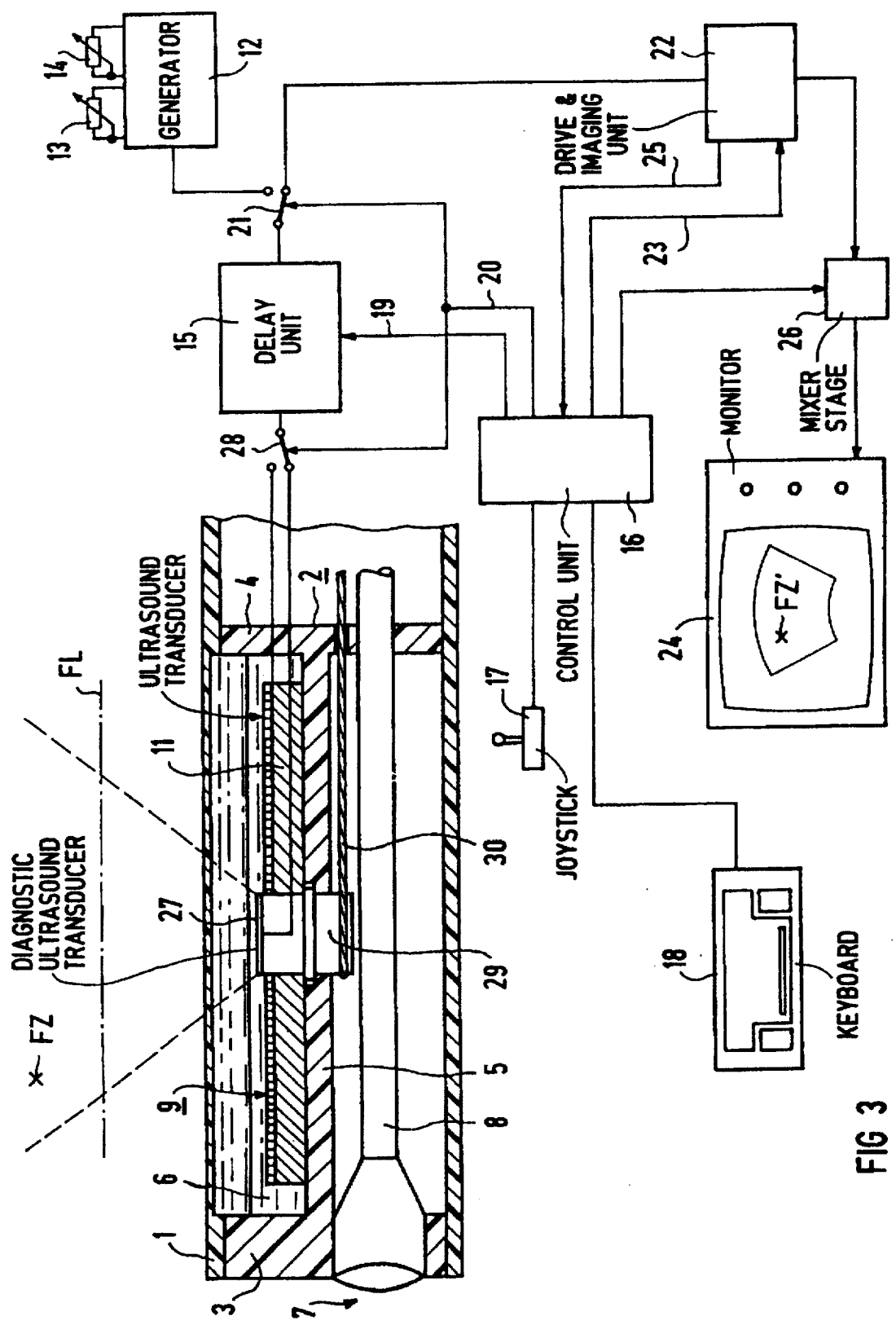
FIG. 3 shows another version of the endoscope of the invention in the same type of representation as in FIG. 1.

The exemplary embodiment of FIG. 3 differs from that set forth above only in that the diagnostic ultrasound required for generating ultrasound images is not emitted and received with the ultrasound transducer 9, but with a separate diagnostic ultrasound transducer 27 that is likewise fashioned as a linear array and that is accepted in a bore extending through the ultrasound transducer 9 and the web 5 of the holder 2. A second switch 28 is therefore present. As the switch 21, the switch 28 is actuated by the control unit 16 via a line 20 and serving the purpose of connecting the ultrasound transducer 9 or the diagnostic ultrasound transducer 27 to the delay unit 15 dependent upon whether the generator 12 or the drive and imaging unit 22 is connected to the delay unit 15 with the switch 21. (Here, too, a separate delay unit can be provided for generating ultrasound images.) Due to the small dimensions of the diagnostic ultrasound transducer 27, a linear scan cannot be undertaken as in the case of the above-described exemplary embodiment, since only an extremely small region could then be imaged. Therefore, a sector scan is implemented in a known way. The limiting lines of the scanned sector are shown with broken lines in FIG. 3 for that case wherein the scanned body slice contains the middle plane FE of the ultrasound transducer 9. Since the carrying member 29 of the diagnostic ultrasound transducer 27 is rotatably seated in the web 5, however, other body slices can also be imaged dependent upon the position in which the ultrasound transducer 27 is turned with a cable pull 30.

For aligning the endoscope in the required way relative to a tissue region to be treated, imaging a tissue region for diagnostic purposes with the diagnostic ultrasound or adjusting the focus zone into the required position with the joystick 17, the production of ultrasound images ensues continuously. During treatment, it is adequate to update the ultrasound image from time to time. It can be provided in this context that the updating of the ultrasound image ensues automatically, for example by the control unit 16 interrupting the treatment and effecting the preparation of an ultrasound image. Alternatively, an operator can enter an instruction for updating the ultrasound image via the keyboard 18.

In the case of the described exemplary embodiments, the ultrasound transducer 9 is arranged inside a space 6 filled with an acoustic propagation medium, this space 6 being partly limited by the outside wall 1 of the endoscope. There is also the possibility, however, of applying the ultrasound transducer onto the outside wall or onto a corresponding part of the endoscope in way that is not shown so that no component part of the endoscope is located between the emission face of the ultrasound transducer and the region to be treated.

Although various minor changes and modifications might be proposed by those skilled in the art, it will be understood that we wish to include within the scope of the patent warranted hereon all such changes and modifications as reasonably come within our contribution to the art.

We caim as our invention:

1. An endoscope comprising:
    a carrier insertable into a living examination subject, said carrier having a leading end which advances into said examination subject;
    optical examination means carried on said carrier for obtaining an image of an interior location in said examination subject and for transmitting said image to an exterior of said examination subject; and
    a source of therapeutic ultrasound including an ultrasound transducer and means for operating said ultrasound transducer to emit therapeutic ultrasound, said ultrasound transducer being disposed at and emitting said therapeutic ultrasound at, said leading end of said carrier.

2. An endoscope as claimed in claim 1 wherein said ultrasound transducer comprises an ultrasound transducer which emits focused therapeutic ultrasound onto a focus zone.

3. An endoscope as claimed in claim 2 further comprising means for displacing said focus zone of said therapeutic ultrasound relative to said carrier.

4. An endoscope as claimed in claim 3 wherein said ultrasound transducer comprises a phased array.

5. An endoscope as claimed in claim 1 further comprising means for emitting and for receiving diagnostic ultrasound.

6. An endoscope as claimed in claim 5 wherein said means for emitting and for receiving diagnostic ultrasound comprises a diagnostic ultrasound transducer separate from said ultrasound transducer of said source of therapeutic ultrasound.

7. An endoscope as claimed in claim 5 wherein said means for emitting and for receiving diagnostic ultrasound comprises said ultrasound transducer of said source of therapeutic ultrasound, and further comprising means for selectively operating said ultrasound transducer to emit said therapeutic ultrasound or to emit and receive said diagnostic ultrasound.

8. An endoscope as claimed in claim 7 wherein said ultrasound transducer comprises a linear array for emitting and receiving said diagnostic ultrasound and wherein said endoscope further comprises means for operating said linear array to conduct a linear scan of said interior location.

9. An endoscope comprising:

a carrier insertable into a living examination subject, said carrier having a leading end which advances into said examination subject;

optical examination means carrier on said carrier for obtaining an image of an interior location in said examination subject and for transmitting said image to an exterior of said examination subject;

a source of therapeutic ultrasound including an ultrasound transducer, said ultrasound transducer, being disposed at said leading end of said carrier, means for operating said ultrasound transducer for emitting said therapeutic ultrasound at said leading end focused to a focus zone; and means for emitting and for receiving diagnostic ultrasound comprising means for generating an ultrasound image of a region in said examination subject containing said focus zone.

10. An endoscope as claimed in claim 9 further comprising means for mixing a mark identifying a current position of said focus zone into said ultrasound image generated using said diagnostic ultrasound.

* * * * *